United States Patent
Ryan

(10) Patent No.: US 9,533,119 B2
(45) Date of Patent: Jan. 3, 2017

(54) METHOD OF FABRICATING AN ELECTRICAL LEAD

(75) Inventor: Garrett Ryan, Surry Hills (AU)

(73) Assignee: CathRX LTD, Homebush Bay, NSW (AU)

( * ) Notice: Subject to any disclaimer, the term of this patent is extended or adjusted under 35 U.S.C. 154(b) by 841 days.

(21) Appl. No.: 13/816,724

(22) PCT Filed: Aug. 12, 2011

(86) PCT No.: PCT/AU2011/001019
§ 371 (c)(1),
(2), (4) Date: Feb. 12, 2013

(87) PCT Pub. No.: WO2012/019230
PCT Pub. Date: Feb. 16, 2012

(65) Prior Publication Data
US 2013/0144224 A1   Jun. 6, 2013

Related U.S. Application Data

(60) Provisional application No. 61/373,723, filed on Aug. 13, 2010.

(51) Int. Cl.
*H01R 43/20* (2006.01)
*A61M 25/00* (2006.01)
(Continued)

(52) U.S. Cl.
CPC ........ *A61M 25/0043* (2013.01); *A61B 5/0422* (2013.01); *A61N 1/0565* (2013.01);
(Continued)

(58) Field of Classification Search
CPC ...... A61N 1/05; A61N 1/0534; A61N 1/0565; A61N 1/3968; H01R 2201/12; Y10T 29/49117; Y10T 29/49002; Y10T 29/49208; Y10T 29/49204; A61B 18/1402
(Continued)

(56) References Cited

U.S. PATENT DOCUMENTS 5,029,585 A   7/1991   Lieber et al.
5,524,337 A   6/1996   Houser et al.
(Continued)

FOREIGN PATENT DOCUMENTS

EP   0007157 A2   1/1980
JP   2006512128 A   4/2006
(Continued)

OTHER PUBLICATIONS

International Preliminary Report on Patentability for International Application No. PCT/AU2011/001019, Feb. 19, 2013, 9 pages.
(Continued)

*Primary Examiner* — Thiem Phan
(74) *Attorney, Agent, or Firm* — TraskBritt

(57) ABSTRACT

A catheter includes a handle, a catheter sheath having at least one conductor within a lumen of the catheter sheath, and a stylet received within the catheter sheath. The catheter sheath is fabricated by providing a tubular member, forming an aperture in a wall of the tubular member at a distal part of the tubular member and inserting a conductor into the lumen of the tubular member. An exposed distal end of the conductor is attached to an electrode, which is then mounted onto an external surface of the tubular member to cover the aperture. The tubular member is then treated by heat to seal the electrode.

12 Claims, 5 Drawing Sheets

(51) Int. Cl.
  *A61B 5/042* (2006.01)
  *A61N 1/05* (2006.01)
  *H01R 24/58* (2011.01)
  *H01R 43/00* (2006.01)
(52) U.S. Cl.
  CPC ............. *H01R 24/58* (2013.01); *H01R 43/00* (2013.01); *H01R 43/20* (2013.01); *A61B 2562/222* (2013.01); *H01R 2201/12* (2013.01); *Y10T 29/49117* (2015.01)
(58) Field of Classification Search
  USPC .......... 29/876, 825, 847, 850; 600/372, 373, 600/374, 393; 607/115, 116, 119, 122
  See application file for complete search history.

(56) References Cited

U.S. PATENT DOCUMENTS

| | | | |
|---|---|---|---|
| 5,855,552 A * | 1/1999 | Houser | ............. A61M 25/0009 600/374 |
| 6,032,061 A | 2/2000 | Koblish et al. | |
| 6,181,971 B1 | 1/2001 | Doan | |
| 7,974,704 B2 * | 7/2011 | Alexander | ............... A61N 1/05 607/115 |
| 8,286,338 B2 * | 10/2012 | Anderson | ............. A61N 1/056 29/825 |
| 2002/0095202 A1 | 7/2002 | Schmidt | |
| 2009/0012591 A1 | 1/2009 | Barker | |

FOREIGN PATENT DOCUMENTS

| | | |
|---|---|---|
| JP | 2007507294 A | 3/2007 |
| JP | 2007185505 A | 7/2007 |
| JP | 2007202727 A | 8/2007 |
| JP | 2013521040 A | 6/2013 |
| NL | WO 2008060142 A1 * | 5/2008 ......... A61B 18/1492 |

OTHER PUBLICATIONS

Search Report of International Patent Application No. PCT/AU2011/001019, mailed Nov. 22, 2011, 5 pages.

Written Opinion of International Patent Application No. PCT/AU2011/001019, mailed Nov. 22, 2011, 8 pages.

Supplemental European Search Report for Application No. EP 11 815 906.0, dated Oct. 31, 2013, 4 pages.

Australian Patent Examination Report No. 1 for Patent Application No. AU 2011288973, dated Aug. 18, 2015, 6 pages.

* cited by examiner

METHOD OF FABRICATING AN ELECTRICAL LEAD

CROSS-REFERENCE TO RELATED APPLICATIONS

This application is a national phase entry under 35 U.S.C. §371 of International Patent Application PCT/AU2011/001019, filed Aug. 12, 2011, designating the United States of America and published in English as International Patent Publication WO 2012/019230 A1 on Feb. 16, 2012, which claims the benefit under Article 8 of the Patent Cooperation Treaty and under 35 U.S.C. §119(e) to U.S. Provisional Patent Application Ser. No. 61/373,723, filed Aug. 13, 2010, the disclosure of each of which is hereby incorporated herein by this reference in its entirety.

TECHNICAL FIELD

This disclosure relates, generally, to an electrical lead and, more particularly, to a method of fabricating an electrical lead and to an electrical lead. The electrical lead is particularly suitable for use as a catheter sheath of a catheter assembly.

BACKGROUND

Any discussion of the prior art throughout the specification should in no way be considered as an admission that such prior art is widely known or forms part of common general knowledge in the field.

In the manufacture of cardiac catheters, a problem arises with an easy, simplified way to attach electrical conductors to electrodes arranged on a catheter sheath of the catheter. It will be appreciated that these conductors need to extend through the catheter sheath to a proximal end of the catheter sheath to be connected to an electrical connector for connection to diagnostic or therapeutic equipment or to a patient cable.

Generally, the manner of connecting the electrodes to the conductors and entraining the conductors within the catheter sheath is very labor intensive. This increases the cost of manufacture of the catheter sheath and, consequently, the cost of the final catheter.

SUMMARY

It is an object of the present invention to overcome or ameliorate at least one of the disadvantages of the prior art or to provide a useful alternative.

In a first aspect, there is provided a method of fabricating an electrical lead that includes:
  providing an elongate tubular member of a non-conductive material, the tubular member defining at least one lumen;
  accessing the at least one lumen externally of the tubular member by forming at least one aperture in a wall of the tubular member proximate a distal end of the tubular member;
  inserting at least one conductor into the at least one lumen of the tubular member via the at least one aperture and feeding the at least one conductor toward a proximal end of the tubular member;
  attaching an electrically conductive element to an exposed distal end of the at least one conductor;
  mounting the at least one electrical conductive element on an external surface of the tubular member; and
  treating the tubular member to close off the aperture.

The tubular member may be a multi-lumen member and the method may include accessing only one of the lumens, a conductor lumen, for inserting a plurality of conductors into the conductor lumen.

In an embodiment, the method may include making a longitudinally extending incision in the wall of the tubular member to form the aperture and to access the conductor lumen and inserting the conductors into the conductor lumen through the incision so that a distal end of each conductor protrudes from the incision.

In another embodiment, the method may include making a plurality of transversely extending apertures in the form of slots in the wall of the tubular member and accessing at least one conductor in the conductor lumen through each slot so that a distal end of each conductor protrudes from its associated slot. The method may include, prior to forming the slots, removing some material from the external surface of the wall of the tubular member.

The method may include attaching proximal ends of the conductors to a feeder device and inserting the feeder device through the conductor lumen to pull the conductors through the conductor lumen.

The method may include attaching an electrically conductive element to each of at least some of the conductors, each electrically conductive element being in the form of a ring electrode, which is a snug fit about the tubular member. Each ring electrode may be attached to its associated conductor by inductively welding (or soldering) the conductor to an inner surface of the ring.

The method may include securing each ring electrode in position on the tubular member. Each ring electrode may be secured in position on the tubular member by a suitable adhesive, which may be an epoxy adhesive. The method may include attaching a tip electrode to the distal end of the tubular member in a similar manner.

The method may include charging a filler material into the conductor lumen to insulate the conductors from each other and to inhibit collapsing of the conductor lumen during subsequent operations. The filler material may be a flexible adhesive that is charged into the conductor lumen and allowed to cure.

The method may include treating the tubular member by heat treatment. Further, the method may include heat treating the tubular member by applying a sacrificial heat shrink at least over the at least one aperture to cause material of the tubular member to melt and to flow together to close the at least one aperture.

The at least one electrically conductive element may stand proud of the external surface of the tubular member after being mounted in the tubular member and the method may include, during heat treatment of the tubular member, causing the tubular member to expand outwardly so that a sealing fillet is formed about each edge of the electrically conductive element.

The method may include, prior to heat treating the tubular member, inserting support elements, for example, mandrels, into the remaining lumens of the tubular member to inhibit collapse of the lumens during the heat treatment operation.

The disclosure extends to an electrical lead fabricated in accordance with the method as described above.

In a second aspect there is provided an electrical lead that includes:
  an elongate tubular member of a non-conductive material, the tubular member defining at least one lumen;

at least one conductor extending through the lumen with a distal end of the conductor protruding through a wall of the tubular member;

an electrically conductive element attached to the distal end of the at least one conductor and the electrically conductive element being mounted on the tubular member to form an electrode on the tubular member; and at least a part of the tubular member adjacent each edge of the electrically conductive element having been treated to be caused to expand outwardly to form a sealing fillet along each edge of the electrically conductive element.

The tubular member may be a multi-lumen member having at least a conductor lumen and a stylet lumen. The tubular member may further define an irrigation fluid lumen. The stylet lumen is eccentrically arranged within the tubular member.

The electrical lead may include a plurality of electrodes, each of which has at least one conductor associated with it, the conductors for the electrodes extending through the conductor lumen of the tubular member and a distal end of each conductor protruding through the wall of the tubular member.

Each electrode may be in the form of a ring with the distal end of the conductor of the electrode attached to an inner surface of the ring. The distal end of the conductor may be attached to the inner surface of its associated electrode by induction welding or soldering.

The wall of the tubular member may be heat treated to close an aperture via that the at least one conductor was accessed from the at least one lumen of the tubular member.

BRIEF DESCRIPTION OF THE DRAWINGS

Preferred embodiments of the invention will now be described, by way of example only, with reference to the accompanying drawings in which.

DETAILED DESCRIPTION

Figure 1:
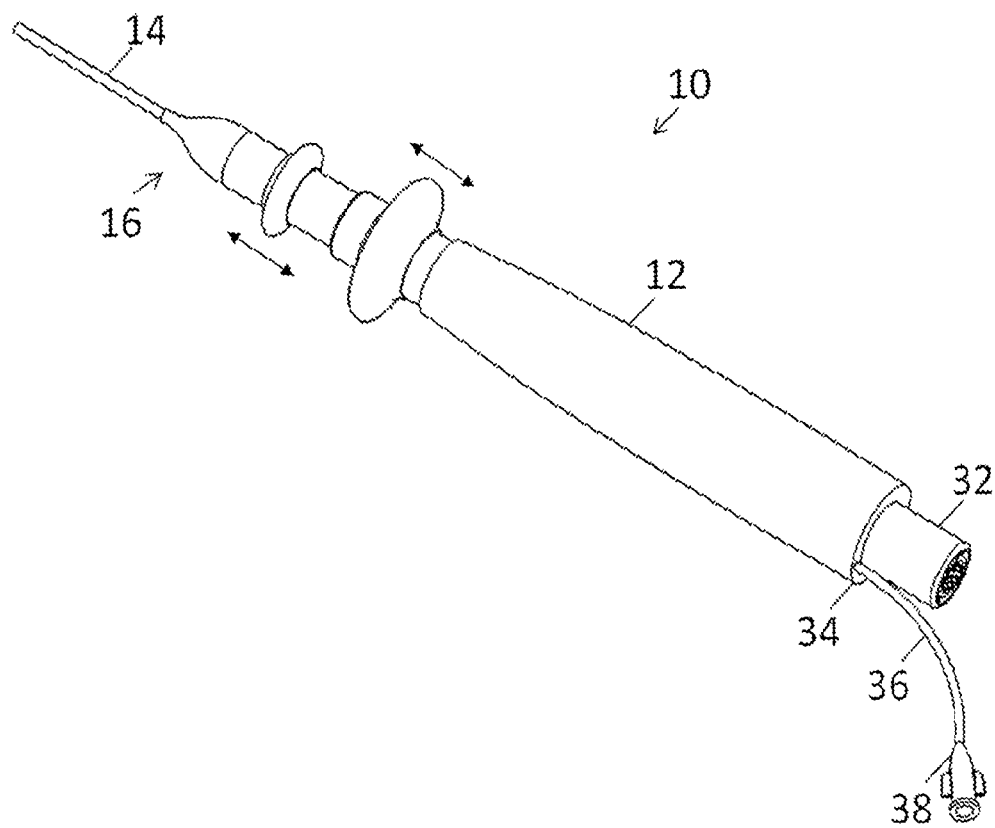
FIG. 1 shows a perspective view of a catheter assembly including an embodiment of an electrical lead forming a catheter sheath of the catheter assembly.
Figure 2:
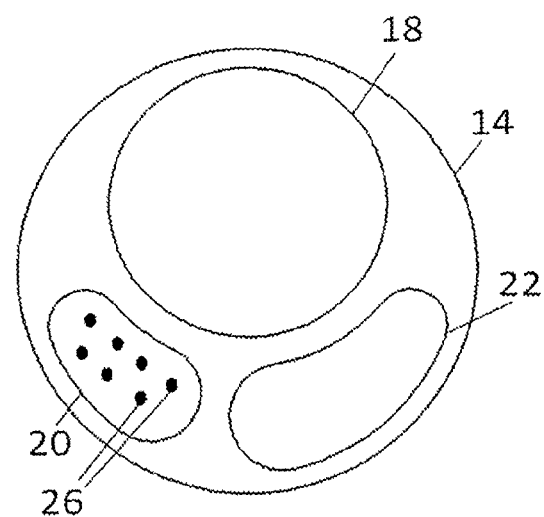
FIG. 2 shows an end view, on an enlarged scale, of a tubular member of the electrical lead.

In FIG. 1 of the drawings, reference numeral 10 generally designates a catheter assembly. The catheter assembly 10 includes a handle 12. A catheter sheath 14, made in accordance with an embodiment of a method of fabricating an electrical lead, extends from a distal end 16 of the handle 12. The catheter sheath 14 defines a plurality of lumens 18, 20 and 22 (FIG. 2). The lumen 18 is a deflection stylet lumen for receiving a deflection stylet. The lumen 20 is a conductor lumen and has a plurality of conductors 26 received therein.

The conductors 26 extend from electrodes 28 (FIG. 8) carried on a distal part 30 of the catheter sheath 14. The conductors 26 extend through the handle 12 to an electrical connector 32 arranged at a proximal end 34 (FIG. 1) of the handle 12.

The lumen 22 is an irrigation lumen for providing irrigating fluid to the electrodes 28 at the distal part 30 of the catheter sheath 14. The lumen 22 communicates with a fluid conduit 36 (FIG. 1). A luer connector 38 is arranged at a proximal end of the conduit 36 for connection to a supply of irrigation fluid (not shown).

Figure 3:
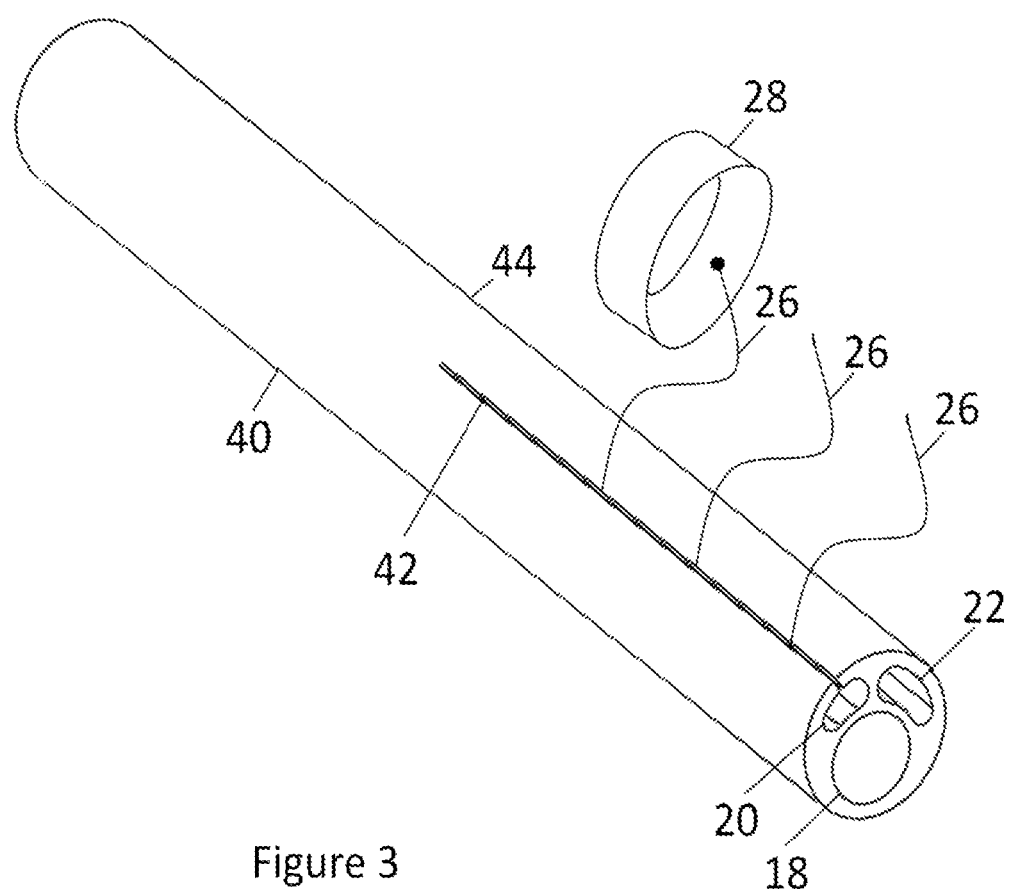
FIG. 3 shows a perspective view of an initial stage in an embodiment of a method of fabricating the electrical lead.

As shown in FIG. 3, in a first embodiment in a method of fabricating an electrical lead for use as the catheter sheath 14, a length of an elongate tubular member 40 is provided. The tubular member 40 is of a biocompatible, non-conductive material such as, for example, a polyether block amide (PEBAX®).

Proximal ends of the conductors 26 are butted up against a threading device, for example, a mandrel (not shown). The proximal ends of the conductors 26 are secured to the mandrel using a sacrificial heat shrink sleeve 50 (see FIG. 7). The mandrel is inserted through the conductor lumen 20 to the proximal end of the tubular member 40 for threading the conductors 26 through the conductor lumen 20.

An incision 42 is formed by cutting the tubular member 40 longitudinally from an outer surface of the tubular member 40 through to the conductor lumen 20. Distal ends of the conductors 26 are pulled through the incision 42 to be externally accessible with a wall 44 of the tubular member 40.

Figure 6:
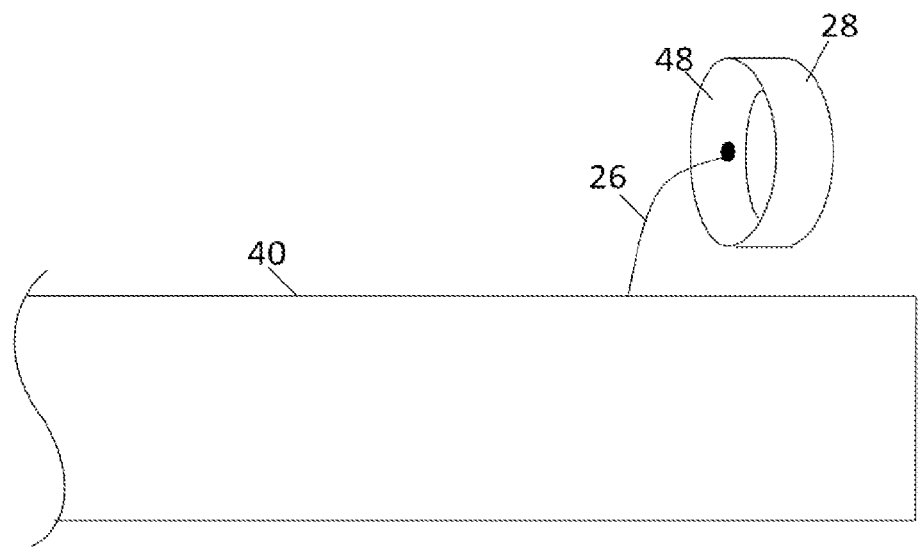
FIG. 6 shows a schematic side view of a step of attaching an electrically conductive element in the method of fabricating the electrical lead.

As illustrated in FIG. 6, in the following step of the method, an electrically conductive element in the form of a ring electrode 28 is attached to a distal end of each conductor 26. The distal end of the conductor 26 is secured to its associated ring electrode 28 by inductively welding an end of the conductor 26 to an internal surface 48 of the ring electrode 28. Induction welding is chosen as it provides a consistent result, no new materials are introduced by the welding of the conductor 26 to the ring electrode 28 and it eliminates the need for any intermediate materials.

Figure 7:
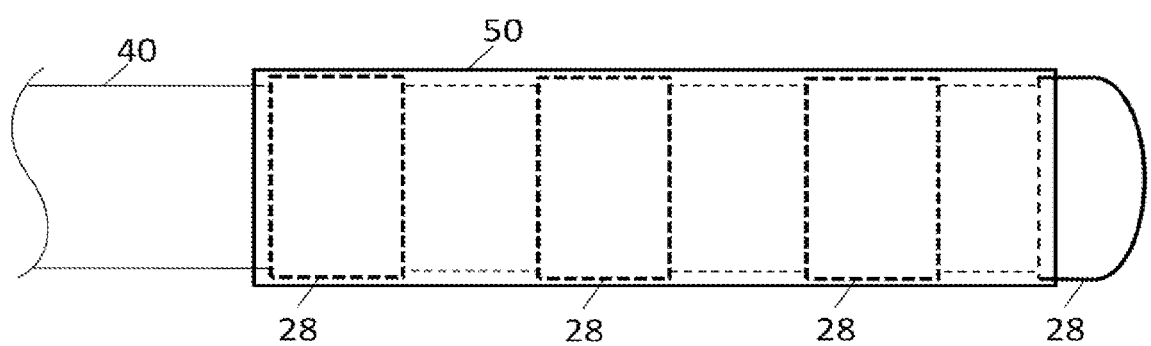
FIG. 7 shows a schematic side view of a step of treating a distal region of the tubular member in the method of fabricating the electrical lead.
Figure 8:
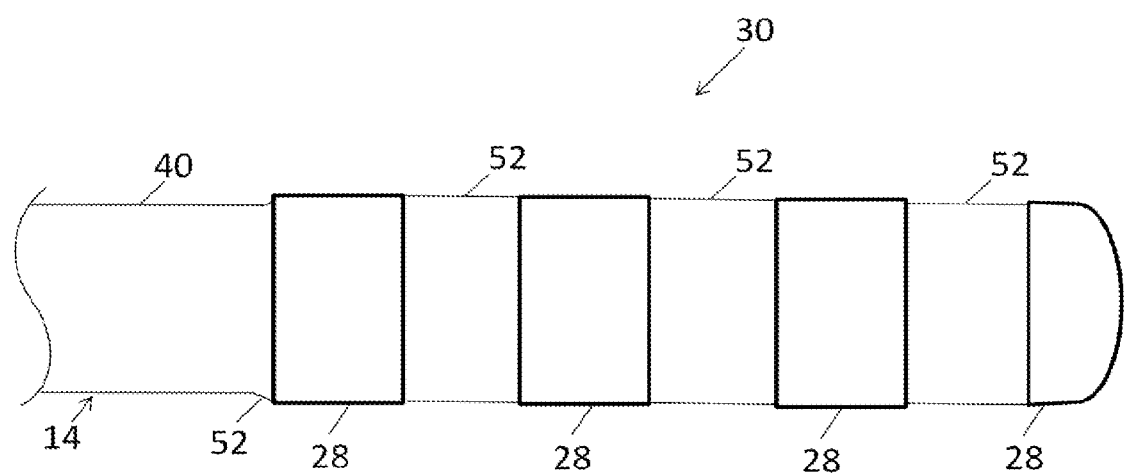
FIG. 8 shows a schematic side view of the distal end of an embodiment of an electrical lead.

The ring electrodes 28 are chosen to have an inner diameter that approximates the outer diameter of the tubular member 40 so each ring electrode 28 is a snug fit about an external surface of the tubular member 40. Once the conductors 26 have been attached to their associated electrodes 28, the ring electrodes 28 are slid over the end of the distal end of the tubular member 40 and positioned at longitudinally spaced intervals as shown in FIGS. 7 and 8 of the drawings. It will be appreciated that any excess length of conductor 26 can be drawn into the conductor lumen 20 of the tubular member 40 by pulling on the proximal end of the conductor 26.

After the ring electrodes 28 have been positioned on the tubular member 40, the end or tip electrode 28 is formed by attaching it to the distal end 30 of the tubular member 40 (FIG. 8).

Once the electrodes 28 have been positioned on the tubular member 40, the conductor lumen 20 is charged with a filler material, which serves to insulate the conductors 26 with respect to each other and to inhibit collapse of the conductor lumen 20 during subsequent steps. The filler material is, for example, a flexible ultraviolet (UV) adhesive.

The electrodes 28 are secured in position on the tubular member 40 by means of a suitable biocompatible adhesive, for example, an epoxy adhesive.

Mandrels are inserted into the irrigation lumen 22 and the stylet lumen 18. This supports the tubular member 40 and retains its integrity by inhibiting collapse of the lumens 18 and 22 during a subsequent heating operation.

A sacrificial heat shrink sleeve 50 is placed over the electrodes 28 as shown in FIG. 7 of the drawings. The distal end of the tubular member 40 is heated using a controlled heat source. Heating of the tubular member 40 causes the material of the tubular member 40 to liquefy to an extent and to flow together causing closure of the incision 42. In addition, radial expansion of the material takes place, the extent of the radial expansion being constrained by the sleeve 50.

After the heat source has been removed, the sacrificial heat shrink sleeve 50 is also removed. As a result of the radial expansion of the material of the tubular member 40, the material adjacent the electrodes 28, as shown at 52 in FIG. 8, expands radially outwardly and molds around the electrodes 28 to seal the edges of the electrodes 28 and make surfaces of the electrodes 28 substantially flush with surfaces of the parts of the material 52 of the tubular member 40. Thus, the expanded material 52 forms a sealing fillet about each edge of the electrodes 28. In so doing, a substantially smooth surface is formed at the end of the now completed catheter sheath 14 and reduces the likelihood of the electrodes 28 snagging on tissue during manipulation of the electrode sheath 14 through the patient's vasculature or in the patient's heart.

Figure 4:
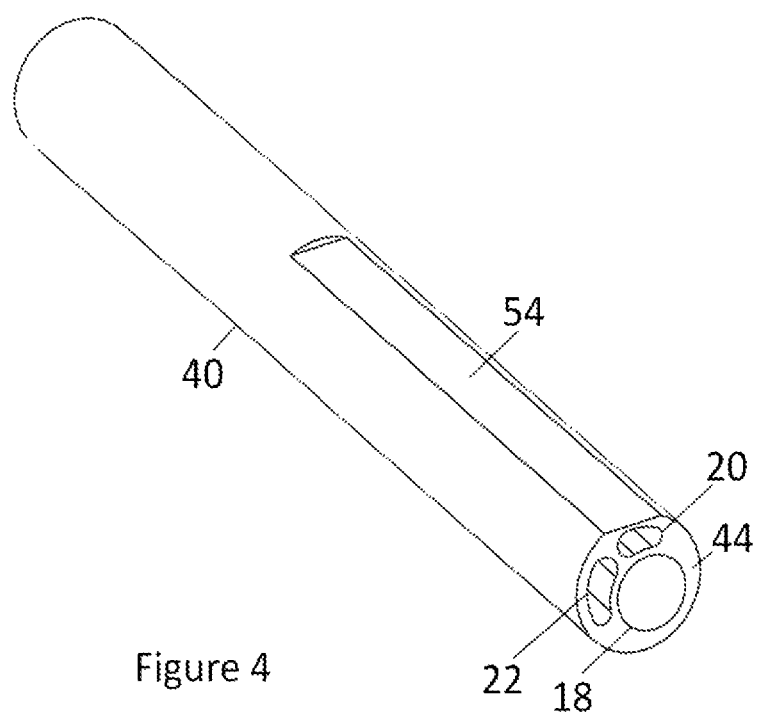
FIGS. 4 and 5 show perspective views of stages in another embodiment of a method of fabricating the electrical lead.
Figure 5:
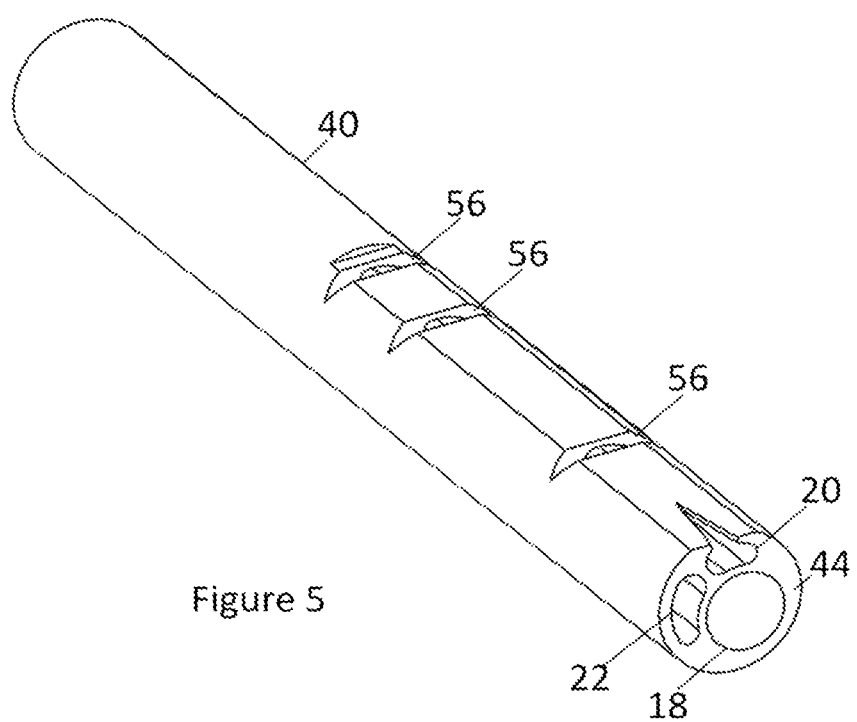

Referring now to FIGS. 4 and 5 of the drawings, a second embodiment of a method of fabricating an electrical lead to provide the catheter sheath 14 is illustrated. With reference to the other drawings, like reference numerals refer to like parts, unless otherwise specified.

In this embodiment, a flat section of the tubular member 40 is machined or skived to provide a land 54 (FIG. 4). After this step, a plurality of transversely extending slots 56, one for each ring electrode 28 (not shown), are formed in the land 54 as shown in FIG. 5 of the drawings. As illustrated, the slots 56 are cut to a sufficient depth to intersect the conductor lumen 20.

In this embodiment, the distal ends of the conductors 26 (FIG. 2) are drawn out of the slots 56 using an appropriate gripping device such as a pair of tweezers or the like. The remaining procedure of forming the catheter sheath 14 is the same as described above with reference to FIGS. 3 and 6-8 of the drawings. The land 54 facilitates the insertion of the adhesive beneath the ring electrodes 28 so that the adhesive is received in the slots 56 to assist in sealing the slots 56.

It is an advantage of the described embodiments that a method of fabricating an electrical lead is provided that simplifies the procedure of producing a suitable catheter sheath. In addition, the use of the heating technique to cause flow of the material of the tubular member assists in sealing the lumens of the tubular member against the ingress of foreign material. This heating technique also serves to assist in retaining the electrodes in position on the tubular member.

Reference throughout this specification to "one embodiment," "some embodiments" or "an embodiment" means that a particular feature, structure or characteristic described in connection with the embodiment is included in at least one embodiment of the present invention. Thus, appearances of the phrases "in one embodiment," "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified, the use of ordinal adjectives "first," "second," "third," etc., to describe a common object, merely indicate that different instances of like objects are referred to, and are not intended to imply that the objects so described must be in a given sequence, either temporally, spatially, in ranking, or in any other manner.

In the appended claims and the description herein, any one of the terms "comprising," "comprised of," or "which comprises" is an open term that means including at least the elements/features that follow, but not excluding others. Thus, the term "comprising," when used in the claims, should not be interpreted as being limitative to the means or elements or steps listed thereafter. For example, the scope of the expression "a device comprising A and B" should not be limited to devices consisting only of elements A and B. Any one of the terms "including," "which includes," or "that includes," as used herein, is also an open term that also means including at least the elements/features that follow the term, but not excluding others. Thus, "including" is synonymous with and means "comprising."

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the appended claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term "coupled," when used in the claims, should not be interpreted as being limited to direct connections only. The terms "coupled" and "connected," along with their derivatives, may be used. It should be understood that these terms are not intended as synonyms for each other. Thus, the scope of the expression "a device A coupled to a device B" should not be limited to devices or systems wherein an output of device A is directly connected to an input of device B. It means that there exists a path between an output of A and an input of B, which may be a path including other devices or means. "Coupled" may mean that two or more elements are either in direct physical or electrical contact, or that two or more elements are not in direct contact with each other but yet still cooperate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the invention.

It will be appreciated by persons skilled in the art that numerous variations and/or modifications may be made to the disclosure as shown in the specific embodiments without departing from the scope of the disclosure as broadly described. The present embodiments are, therefore, to be considered in all respects as illustrative and not restrictive.

The claims defining the invention are as follows:

1. A method of fabricating an electrical lead, comprising:
   providing an elongate multi-lumen tubular member of a non-conductive material, the tubular member defining a plurality of lumens including a conductor lumen;
   accessing the conductor lumen externally of the tubular member by making a longitudinally extending incision in a wall of the tubular member to form at least one aperture in the wall of the tubular member proximate a distal end of the tubular member and to access the conductor lumen;
   inserting a plurality of conductors into the conductor lumen through the incision and feeding the plurality of conductors toward a proximal end of the tubular member so that a distal end of each conductor protrudes from the incision;
   attaching at least one electrically conductive element to an exposed distal end of at least one conductor of the plurality of conductors;
   mounting the at least one electrically conductive element on an external surface of the tubular member; and
   treating the tubular member to close off the at least one aperture.

2. The method of claim 1, further comprising making a plurality of transversely extending apertures in the form of slots in the wall of the tubular member, and accessing at least one conductor of the plurality of conductors in the conductor lumen through each slot so that a distal end of the at least one conductor protrudes from its associated slot.

3. The method of claim 2, further comprising, prior to forming the slots, removing some material from the external surface of the wall of the tubular member.

4. The method of claim 1, further comprising attaching proximal ends of the plurality of conductors to a feeder device and inserting the feeder device through the conductor lumen to pull the plurality of conductors through the conductor lumen.

5. The method of claim 4, further comprising securing each ring electrode in position on the tubular member.

6. The method of claim 1, further comprising attaching an electrically conductive element to each of at least some of the plurality of conductors, each electrically conductive element being in the form of a ring electrode configured to fit snugly about the tubular member.

7. The method of claim 6, wherein each ring electrode is attached to its associated conductor of the plurality of conductors by inductively welding the conductor to an inner surface of the ring electrode.

8. The method of claim 1, further comprising charging a filler material into the conductor lumen to insulate the plurality of conductors from each other and to inhibit collapsing of the conductor lumen.

9. The method of claim 1, further comprising heat treating the tubular member.

10. The method of claim 9, wherein heat treating the tubular member comprises applying a sacrificial heat shrink at least over the incision and causing material of the tubular member to melt and to flow together to close the incision.

11. The method of claim 10, wherein the at least one electrically conductive element stands proud of the external surface of the tubular member after being mounted in the tubular member, and wherein the method further comprises, during heat treatment of the tubular member, causing the tubular member to expand outwardly so that a sealing fillet is formed about each edge of the at least one electrically conductive element.

12. The method of claim 9, further comprising, prior to heat treating the tubular member, inserting support elements into lumens of the tubular member other than the conductor lumen to inhibit collapse of other lumens during the heat treating.

* * * * *